(12) United States Patent
McPhail

(10) Patent No.: US 11,083,860 B2
(45) Date of Patent: Aug. 10, 2021

(54) CPAP MASK CUSHION COVER

(71) Applicant: Rita McPhail, Battle Creek, MI (US)

(72) Inventor: Rita McPhail, Battle Creek, MI (US)

( * ) Notice: Subject to any disclaimer, the term of this patent is extended or adjusted under 35 U.S.C. 154(b) by 251 days.

(21) Appl. No.: 16/205,912

(22) Filed: Nov. 30, 2018

(65) Prior Publication Data
US 2019/0160248 A1   May 30, 2019

Related U.S. Application Data

(60) Provisional application No. 62/592,793, filed on Nov. 30, 2017.

(51) Int. Cl.
*A61M 16/06* (2006.01)
*D04B 1/22* (2006.01)
*A61M 16/00* (2006.01)

(52) U.S. Cl.
CPC .... *A61M 16/0611* (2014.02); *A61M 16/0003* (2014.02); *A61M 16/0616* (2014.02); *D04B 1/22* (2013.01); *A61M 2205/0216* (2013.01); *A61M 2205/0238* (2013.01); *A61M 2207/00* (2013.01); *D10B 2509/00* (2013.01)

(58) Field of Classification Search
CPC .. A61M 16/00; A61M 16/06; A61M 16/0605; A61M 16/0611; A61M 16/0616; A61M 16/0622; A61M 2205/0216; A61M 2205/0238; A61M 2207/00; D04B 1/22; D04B 1/24; D10B 2509/00; A62B 18/00
See application file for complete search history.

(56) References Cited

U.S. PATENT DOCUMENTS

| | | | | |
|---|---|---|---|---|
| 6,698,427 | B1* | 3/2004 | Glowers | A61M 16/06 128/200.24 |
| 9,308,343 | B2* | 4/2016 | Groll | A61M 16/0694 |
| 2002/0162556 | A1* | 11/2002 | Smith | A61B 5/6803 128/207.12 |
| 2008/0142015 | A1* | 6/2008 | Groll | A61M 16/125 128/206.24 |
| 2009/0188507 | A1* | 7/2009 | LaCava | A61M 16/0666 128/207.13 |
| 2011/0253144 | A1* | 10/2011 | Groll | A61M 16/125 128/206.24 |
| 2012/0204881 | A1 | 8/2012 | Davidson | |
| 2014/0209098 | A1* | 7/2014 | Dunn | A61M 16/0683 128/206.21 |
| 2014/0251334 | A1* | 9/2014 | Kramer | A61M 16/0875 128/205.25 |
| 2016/0213872 | A1* | 7/2016 | Paulk | A61M 16/0875 |

(Continued)

*Primary Examiner* — Joseph D. Boecker
(74) *Attorney, Agent, or Firm* — The Dobrusin Law Firm, PC

(57) ABSTRACT

A CPAP mask cover and method for making the same are presented. The CPAP mask cover includes first and second material sections arranged in different orientations, such as with the bias of the first material section substantially perpendicular to the bias of the second material section. A first and second seam and opposite ends of the cover connect the first and second material sections along an overlap or abutment of the inner edges of the first and second material sections. A portion of the edges of the first and second material sections between the first and second seams remain unconnected and capable of forming an opening when the mask cover is stretched to fit onto a CPAP mask.

11 Claims, 6 Drawing Sheets

(56) References Cited

U.S. PATENT DOCUMENTS

2017/0290376 A1* 10/2017 Maheshwari ............ A41C 3/12
2017/0312466 A1* 11/2017 Manning ........... A61M 16/0616
2018/0043120 A1* 2/2018 Hunley .................... A41C 3/12

* cited by examiner

CPAP MASK CUSHION COVER

CROSS-REFERENCE TO RELATED APPLICATIONS

The present application claims priority to U.S. Provisional Patent Application No. 62/592,793 filed on Nov. 30, 2017 and entitled "CPAP MASK COVER," the contents of which are hereby incorporated in their entirety.

FIELD OF INVENTION

The present invention generally relates to a cover for a continuous positive airway pressure ("CPAP") mask and a method for making the same.

BACKGROUND

Obstructive sleep apnea syndrome (commonly referred to as obstructive sleep apnea) is a medical condition that includes a symptom of repeated and prolonged episodes of cessation of breathing throughout the night during sleep. This is generally a condition in which a person's airway becomes blocked or restricted due to the over-relaxation of the muscles and tissues in the throat. A restrictive air supply impairs the oxygen flow to the lungs and, in turn, to the brain.

Individuals with sleep apnea may stop breathing, or suffer an apnea, on a plurality of occasions of typically 10 to 30 times an hour during sleep. The apneas are generally followed by sudden reflexive attempts to breathe. As a result, the individual suffering from sleep apnea experiences fragmented sleep. Such sleep may result in daytime drowsiness, headaches, weight gain, limited attention span, memory loss, lethargy, inability to maintain concentration and/or depression. Sleep apnea has also been linked to more serious medical conditions, such as increased hypertension and greater risk of stroke, heart disease, and diabetes, if left untreated.

Effective treatment of sleep apnea requires the airway to remain open during sleep. Modern respiratory therapy utilizes a continuous positive airway pressure ("CPAP") machine and a ventilation interface worn during sleep in order to keep the airways open. A variety of CPAP machines can provide this treatment. All positive airway pressure machines use an interface to deliver ambient air, under pressure, to the patient's airway. This interface commonly consists of a mask 10, such as a full-face mask that covers both the nose and mouth that is connected to the CPAP machine by way of an air hose 16, as shown in FIGS. 1 and 2. The mask 10 includes a cushion, such as a silicon cushion 12 that contacts the face of the individual around the nose and mouth. The silicon cushion 12 is intended to provide a soft and comfortable interface between the mask 10 and the face while also providing a seal between the mask 10 and the individual's skin. In addition to CPAP masks, masks for other machines, such as BIPAP, ventilators, and respirators also employ similar cushions that are configured to engage the user's face around the mouth.

For some patients, especially those with sensitive skin, the silicon cushion 12 may cause redness, irritation, or even blisters when worn throughout the night. However, finding a suitable medium to place between the silicon and the skin is difficult for several reasons. First, any material placed between the skin and the cushion 12 must allow airflow through the mask. Second, the material must be able to stay in place. And finally, the material must maintain its shape to not block any airflow, all while not being irritable to sensitive skin.

In addition, many CPAP, ventilator, and respirator masks suffer from issues such as a defective seal between the mask cushion and the user's skin which leads to leaking and sliding. These issues may also be caused by oiliness of the skin, sweat, or uncomfortableness of the user.

Accordingly, an improved CPAP mask cover and method for making the same is needed.

SUMMARY

A CPAP mask cover and method for making the same are generally presented. The CPAP mask cover may comprise a first material section and a second material section, wherein the second material section is oriented differently than the first material section. A first seam connecting the first and second material sections may be formed along an abutment or overlap of the first and section material section edges. The first seam may be located along a portion of the abutment or overlap at or near a first end of the first and second material sections. Similarly, a second seam connecting the first and second material sections may be formed along an abutment or overlap of the first and section material section edges. The second seam may be located along a portion of the abutment or overlap at or near a second end, opposite the first end, of the first and second material sections. A portion of the edges of the first and second material sections between the first and second seams may remain unconnected and capable of forming an opening when the mask cover is stretched.

In an embodiment, the method of making a CPAP mask cover may comprise the steps of: providing a pattern for cutting sections of a material; cutting a first material section having a first orientation; cutting a second material section having a second orientation different from the first orientation of the first material section; arranging the first and second material sections such that an inner edge of the first material section abuts or overlaps an inner edge of the second material section; forming a first seam along the abutment or overlap of the first and second material sections, wherein the first seam is located along a portion of the abutment or overlap at or near a first end of the CPAP mask cover; and forming a second seam along the abutment or overlap of the first and second material sections, wherein the second seam is located along a portion of the abutment or overlap at or near a second end of the CPAP mask cover, opposite the first end. A portion of the inner edges of the first and second material sections between the first and second seams may remain unconnected and capable of forming an opening when the mask cover is stretched.

In an embodiment, the orientation of the first and second material sections may be substantially perpendicular to one another. The material sections may be formed of a jersey or knit material having a measurable elasticity and including a straight grain and a cross grain. The straight grain and the cross grain may be substantially perpendicular, and a bias may be be measured as 45 degrees between the straight grain and the cross grain. The bias of the first material section may be oriented substantially perpendicular to the bias of the second material section.

In an embodiment, the CPAP mask cover may include an elastic band located at or near an outer edge of the CPAP mask cover. The elastic band may be sewn into the material and configured to affix the cover to a CPAP mask.

BRIEF DESCRIPTION OF THE DRAWINGS

The operation of the invention may be better understood by reference to the detailed description taken in connection with the following illustrations, wherein.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
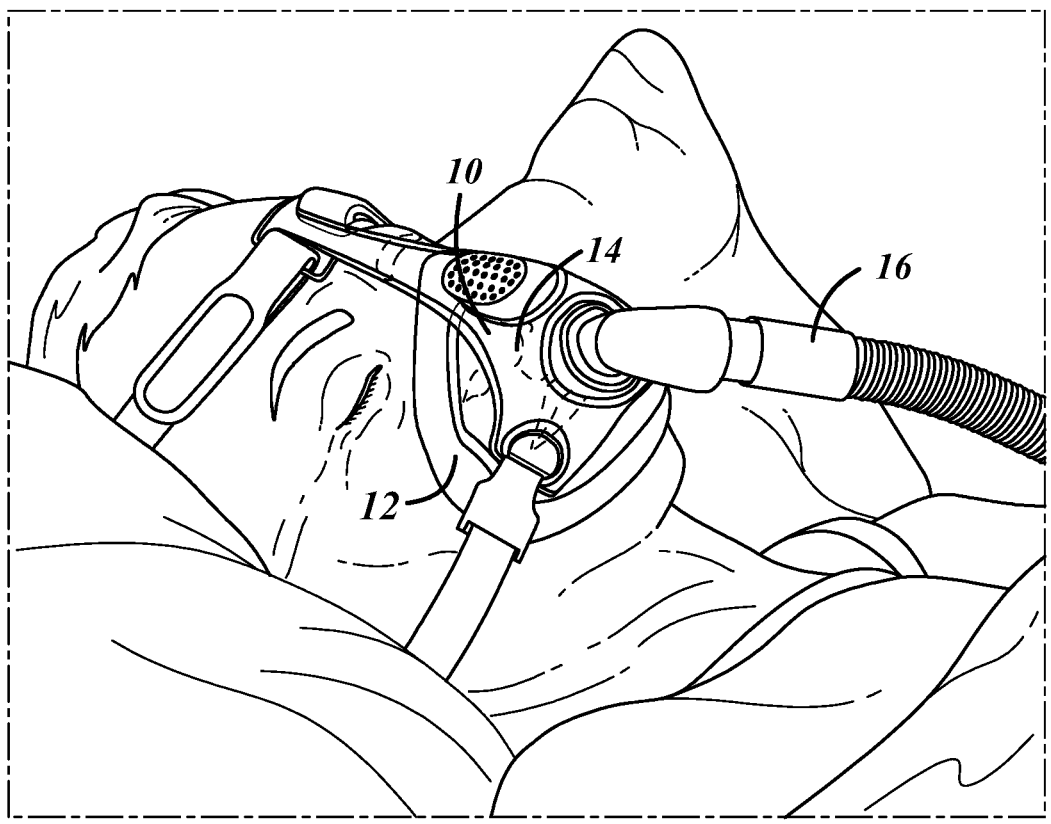
FIG. 1 illustrates a patient wearing a traditional CPAP mask.
Figure 2:
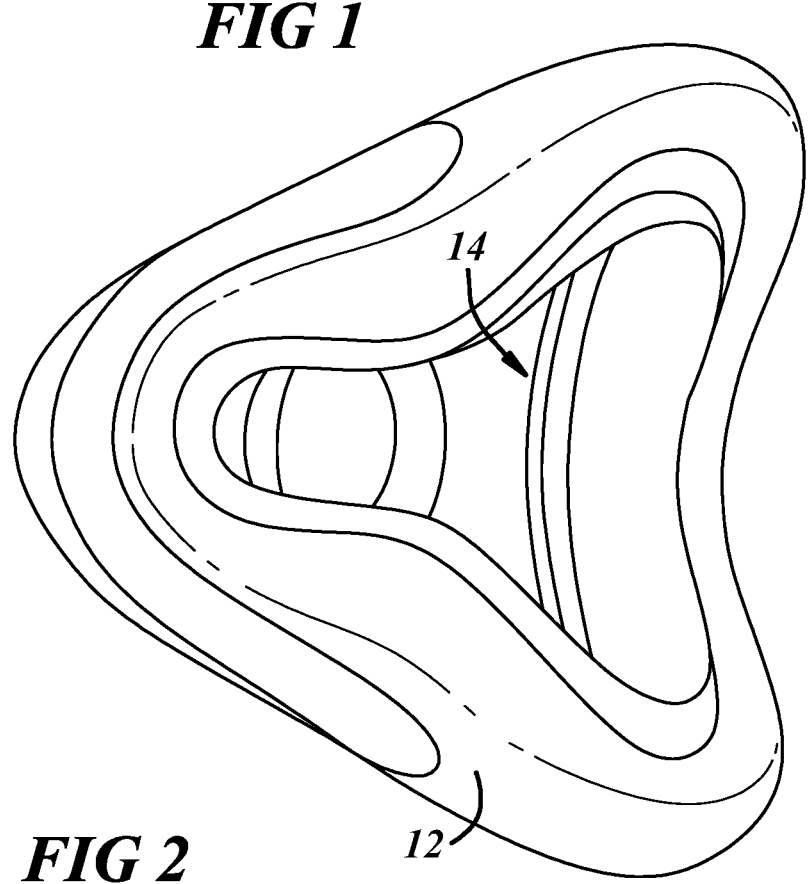
FIG. 2 illustrates a top view of a traditional CPAP mask having a silicon cushion.
Figure 3:
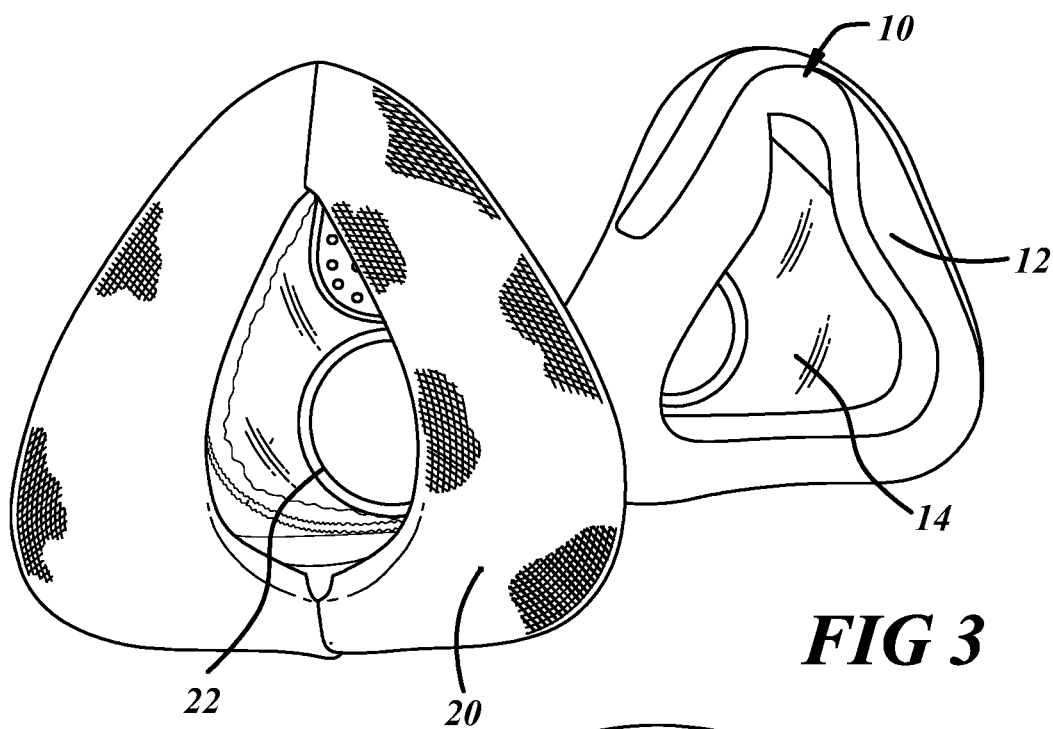
FIG. 3 illustrates a CPAP mask having a CPAP mask cover thereon next to a traditional CPAP mask.

A CPAP mask cover 20 and method of making the same are generally presented. The CPAP mask cover may be designed to generally cover a traditional CPAP mask, such as a mask designed to cover the nose and mouth of a user as shown in FIGS. 1 and 2. However, it will be appreciated that the mask cover 20 may be designed to fit or work with any style of CPAP mask or other type of facial mask.

The CPAP mask cover 20 may be formed on any appropriate material, such as a knit or jersey material, which unlike woven material, has a degree of stretchiness to it depending on which direction it is pulled. The material may include a straight grain and a cross grain to form a bias grain ("the bias"), commonly measured at 45 degrees to the perpendicular straight and cross grains. Portions of the mask cover 20 may be arranged with specific orientation of the grain or bias with respect to other portions of the mask cover 20, as described in further detail below.

In an embodiment, the CPAP mask cover 20 may be configured to fit over a traditional CPAP mask 10 designed to cover a user's mouth and nose. The CPAP mask 10 may include a frame 14 and a cushion 12 connected to the frame 14 and designed to form a seal with the face of a user. The cushion 12 may be comprised of any appropriate material or materials, such as silicon, to provide a soft padded interface with the mask 10 but also have the ability to form a tight seal to maintain a vacuum and air pressure. The frame 14 may include one or more openings to connect to a hose 16 and receive pressurized airflow therethrough.

The CPAP mask cover 20 may be designed to fit over or around the cushion 12 to provide a barrier between the user's skin and the silicon cushion 12. For example, as shown in the FIGS, the mask cover 20 may be generally sized and shaped to match the size and shape of the mask 10. The cover 20 may include an opening 22 centrally located to allow airflow from the mask 10 through the cover 20. The cover 20 may further be secured to the mask 10 and designed to resist deformation, as further described below.

Figure 4:
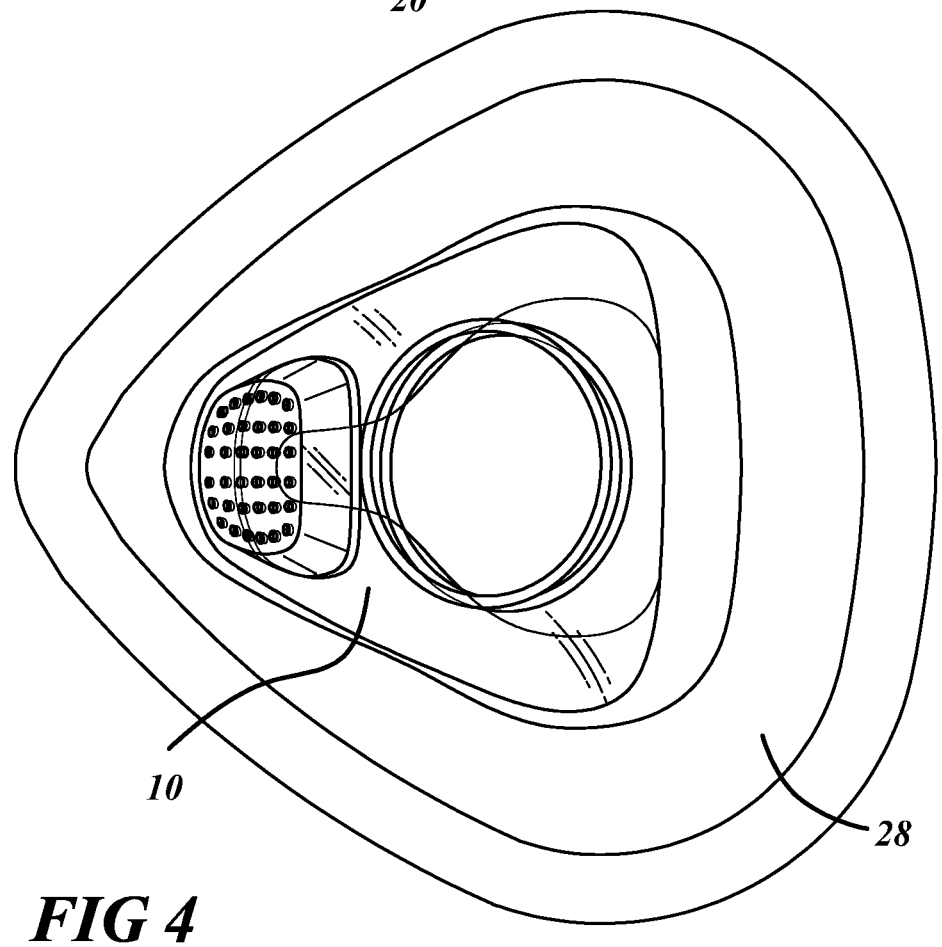
FIG. 4 illustrates a CPAP mask and corresponding pattern.
Figure 5:
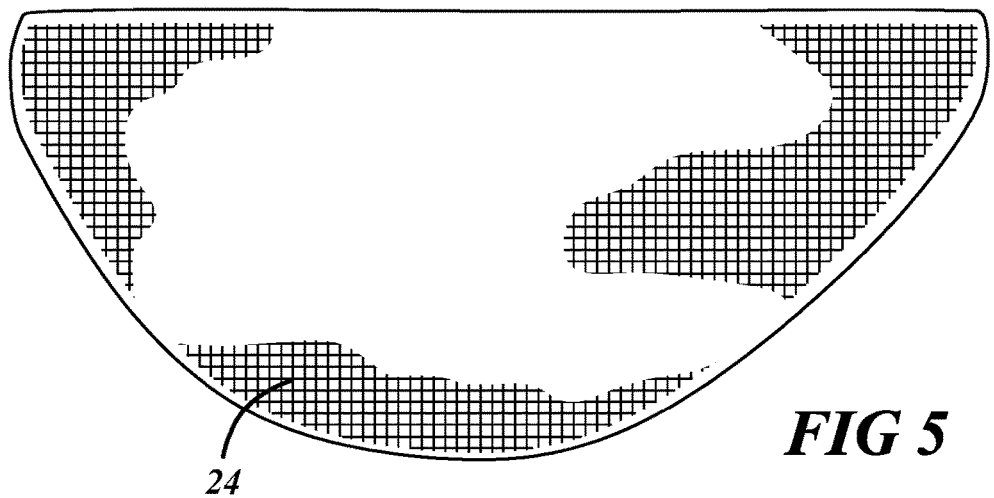
FIG. 5 illustrates a first half of a CPAP mask cover.

In an embodiment, the mask cover 20 may be formed of two separate halves of material 24, 26. The halves 24, 26 may be cut from a pattern that is of similar size and shape to the entire mask 10, such as the pattern 28 shown in FIG. 4. The halves 24, 26 may be generally equivalent in size and shape and mirror one another. The halves 24, 26 may be arranged in a desired configuration, described below, and stitched or sewn together to form the mask cover 20.

Figure 6:
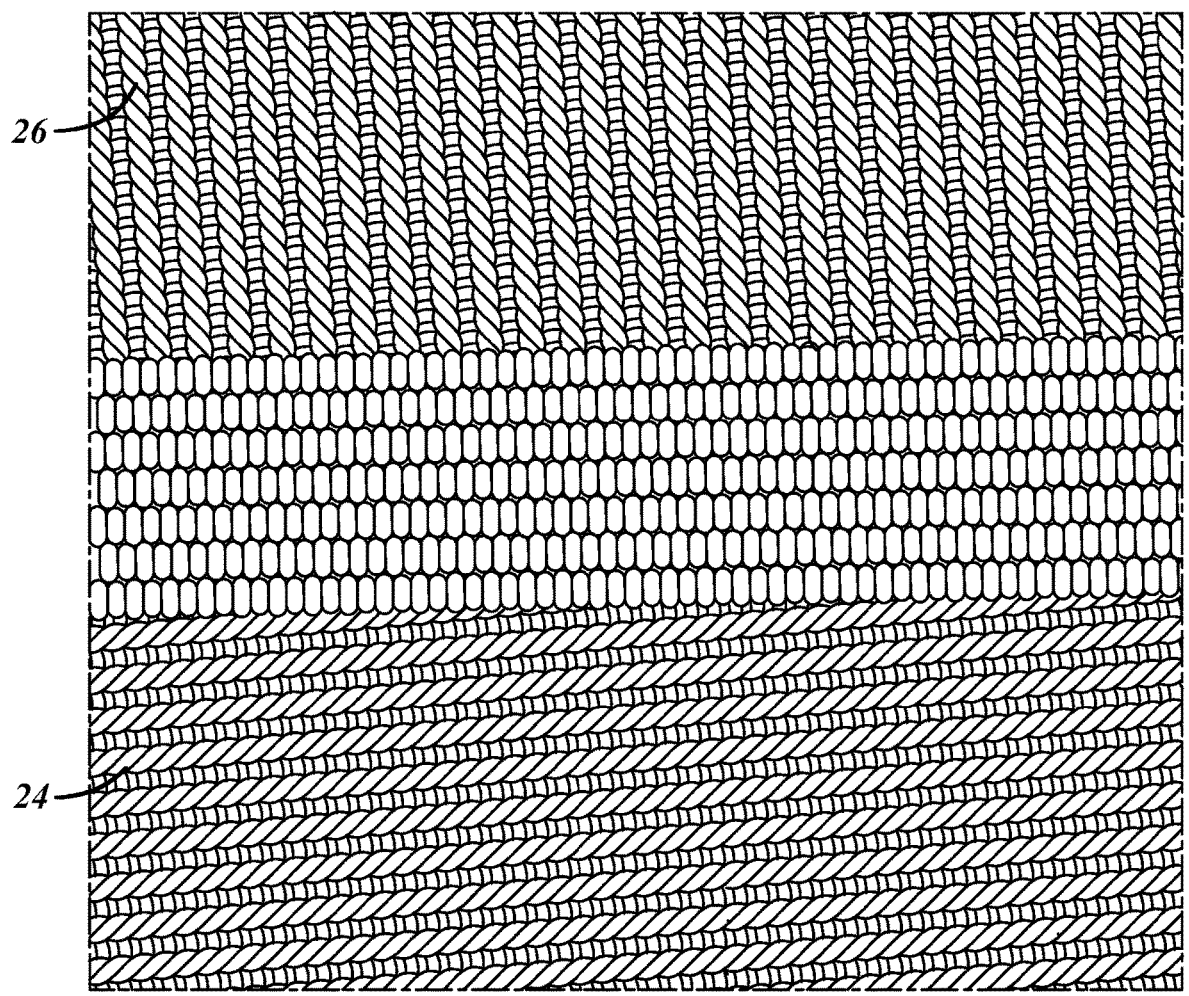
FIG. 6 illustrates a first half of a CPAP mask cover fabric having a vertical or lengthwise grain adjacent to a second half of a CPAP mask cover fabric having a horizontal or crosswise grain.

In an embodiment, the first and second halves 24, 26 of the mask cover 20 may be oriented with the grain of the first half 24 arranged at a given angle, such as approximately or substantially perpendicular, to the grain of the second half 26. For example, as shown in FIG. 6, the first and second halves 24, 26 may each be formed of a knitted material having a measurable elasticity. The first half 24 may be cut with a vertical grain and the second half 26 may be cut with a horizontal grain. However, it will be appreciated that other orientations of the grain in the first and second halves 24, 26 may be used that also produce the relative difference in orientation. When the first and second halves 24, 26 are connected to form the mask cover 20 the grains of the halves may be approximately perpendicular to one another. This arrangement may help to prevent the mask cover 20 from deforming or losing its shape once it is attached to the cushion 12.

Figure 10:
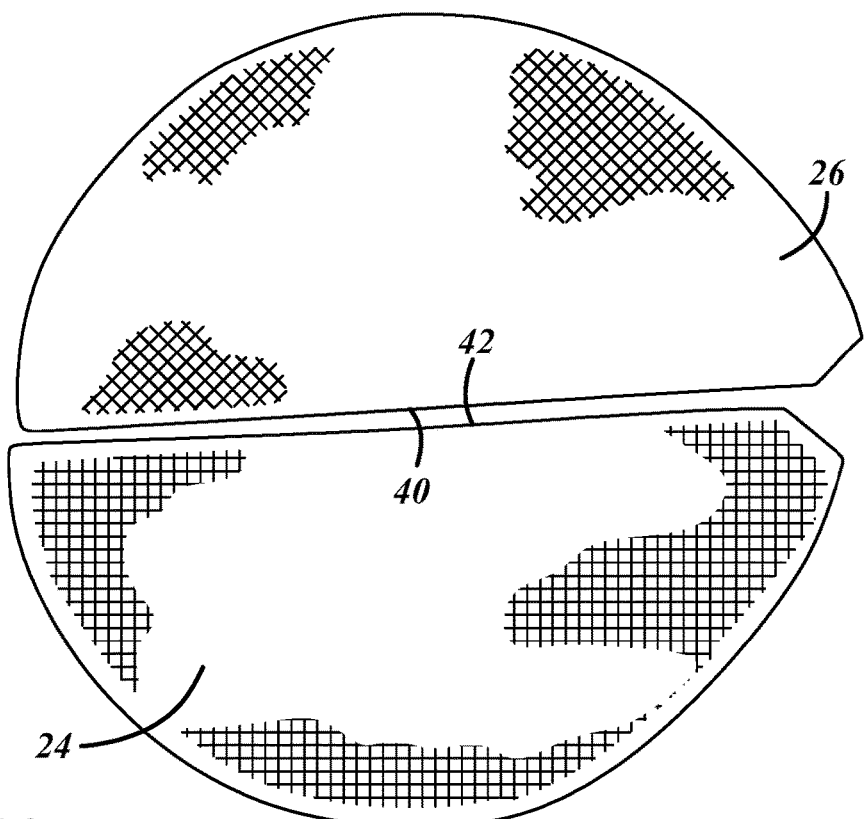
FIG. 10 illustrates a first half of a CPAP mask cover fabric arranged with its bias at a first angle adjacent to a second half of a CPAP mask cover fabric arranged with its bias at a second angle.

In an embodiment, the first and second halves 24, 26 of the mask cover 20 may be oriented with the bias of the first half 24 arranged at a given angle with respect to the bias of the second half 26, such as with the bias of the first half 24 approximately or substantially perpendicular to the bias of the second half 26. For example, as shown in FIG. 10, the first half 24 may be arranged with grain in a first direction and the second half 26 may be arranged with the grain in a second direction, perpendicular to the grain of the first half 24 when the two halves 24, 26 are mated together.

Figure 7:
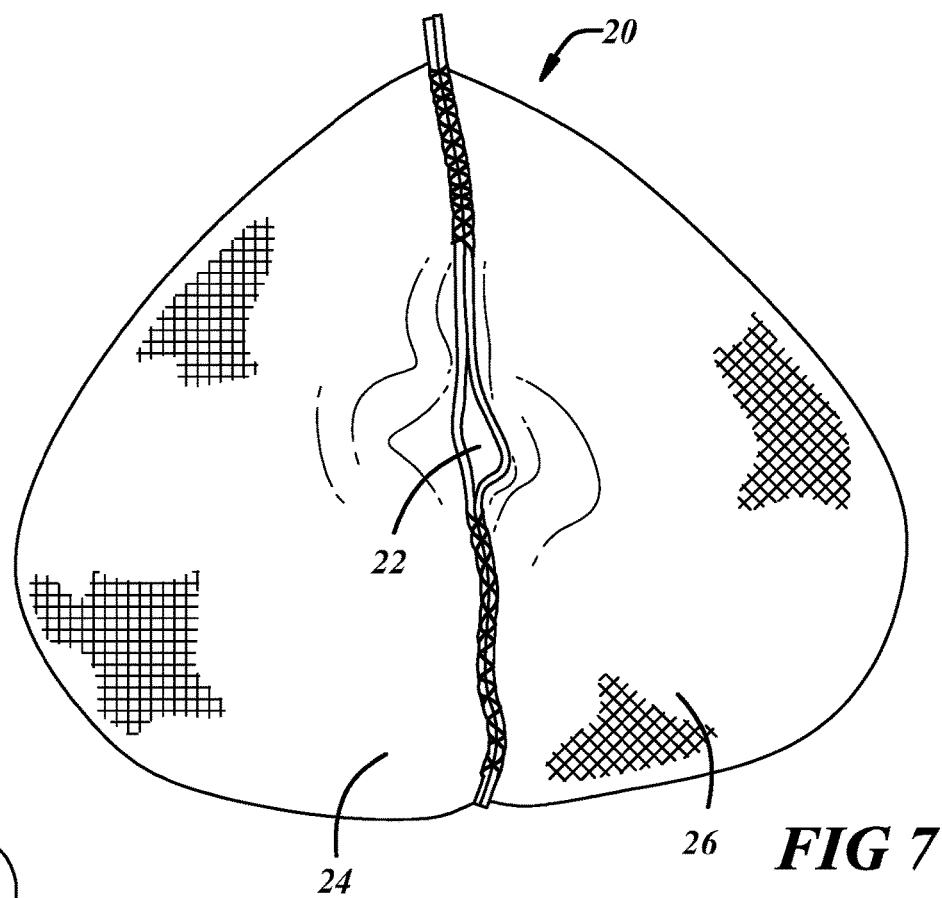
FIG. 7 illustrates two halves of a CPAP mask cover sewn together to form a full CPAP mask cover.

The two halves 24, 26 may be connected together in a manner that allows an opening between them for airflow from the mask 10 through the cover 20. For example, as illustrated in FIG. 7, the two halves 24, 26 may be sewn or stitched together at a top end and bottom end and may be left unconnected in between the sewn or stitched portions. The halves 24, 26 may be aligned to abut or overlap their respective inner edges 40, 42 such that a connection seam 34 may be sewn or stitched to connect the two halves 24, 26 together at both a top portion and bottom portion of the material. The unconnected edges of the first and second halves 24, 26 may pull apart from each other when the cover 20 is connected to a mask 10 to allow for air to pass through the cover 20.

Figure 11:
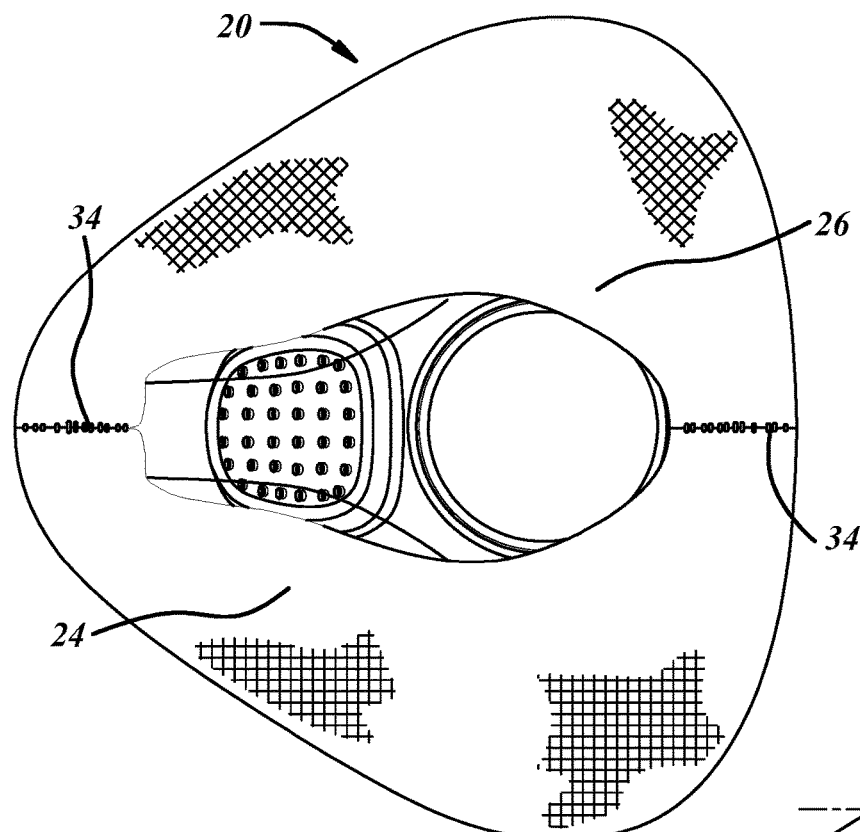
FIG. 11 illustrates a zoomed in view of a seam connected two halves of a CPAP mask having their bias arranged at an angle to one another.
Figure 12:
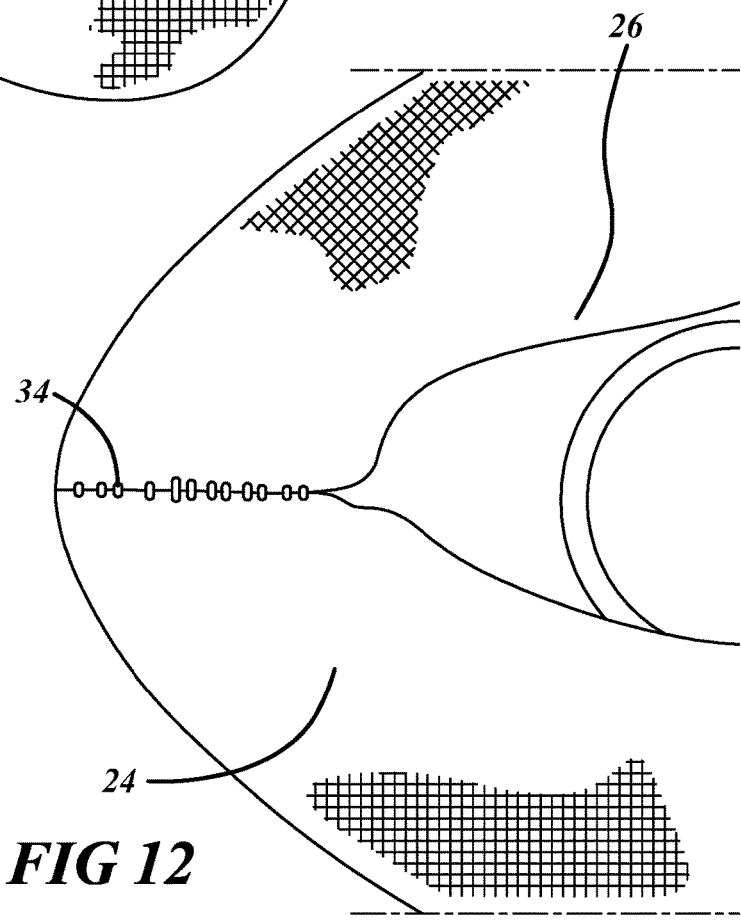
FIG. 12 illustrates a zoomed out view of a seam connected two halves of a CPAP mask having their bias arranged at an angle to one another.

The arrangement of the two halves 24, 26 with the grain or bias oriented perpendicular to one another, along with the material selection, can provide numerous advantages over prior designs. One advantage is that the orientation of the grain or bias along the half cut lines may help the cover 20 to maintain its shape. Specifically, as shown in FIGS. 11 and 12, the orientation of the bias or grain along with the seam 34 connecting the two halves 24, 26 together may reduce the stretchiness of the fabric of the cover 20 and help the cover to maintain the opening hole for the user's mouth. By contrast, other products may sag or loosen over time allowing the mouth hole to close and reduce ease of breathing for the user.

The mask cover 20 may include an elastic band 30 so secure the mask cover 20 to the mask 10. The elastic band 30 may be sewn into the cover 20 and stretchable to allow the cover to surround the cushion 12 and attach thereto. The elastic band 30 may be located at or near an outer edge of the CPAP mask cover and may be stretched over a portion of the CPAP mask to connect thereto.

Figure 8:
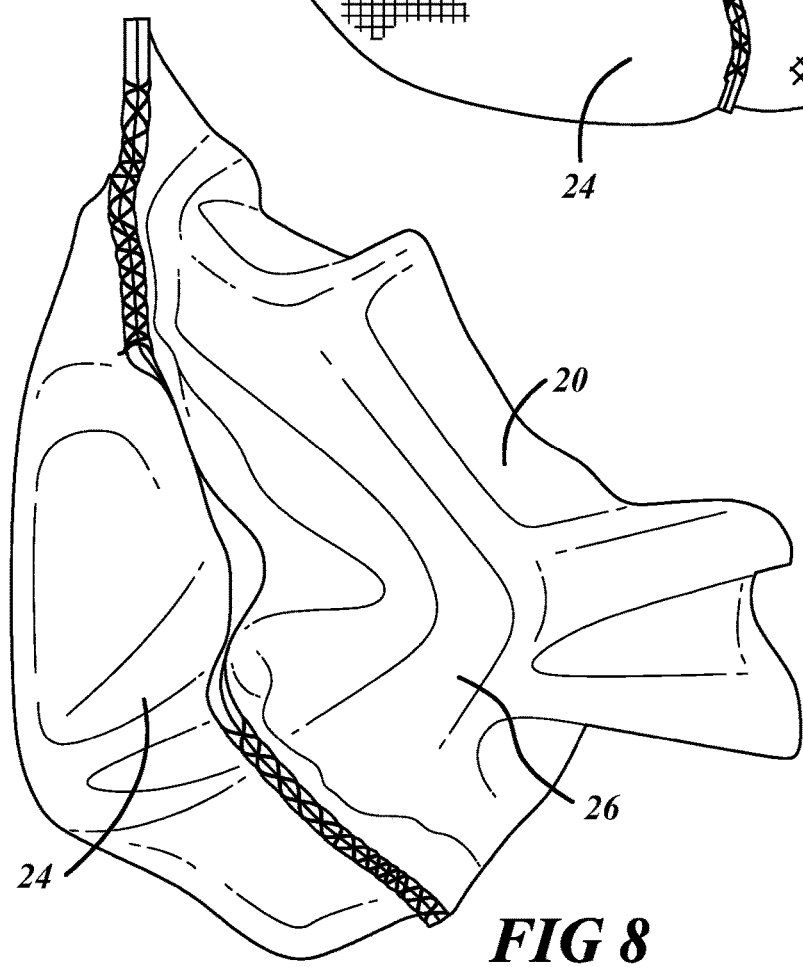
FIG. 8 illustrates a CPAP mask cover placed over the silicon cushion of a CPAP mask.
Figure 9:
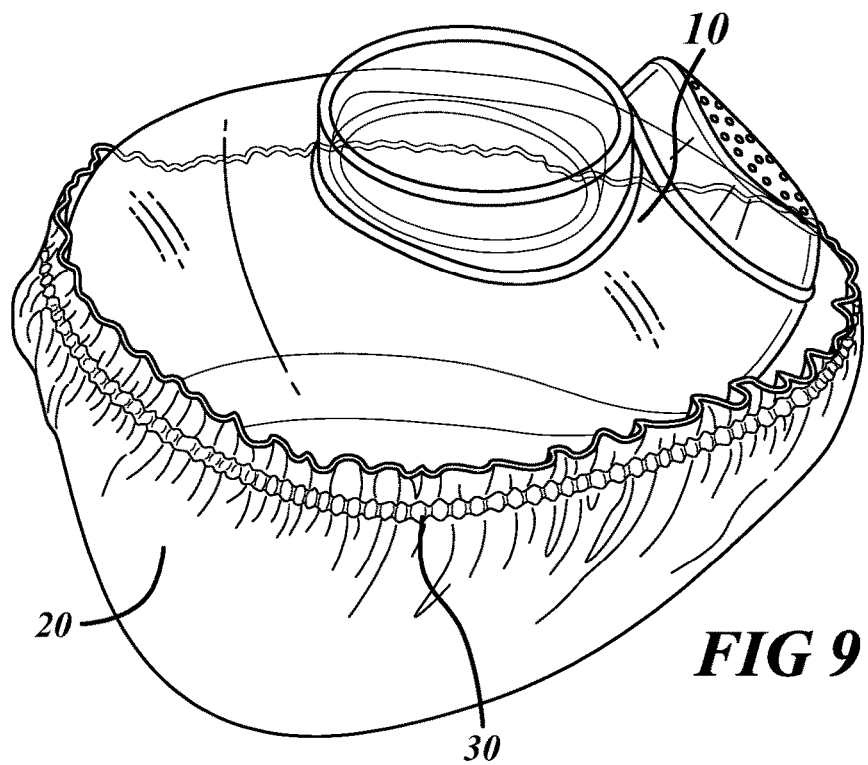
FIG. 9 illustrates a CPAP mask cover affixed to a CPAP mask by an elastic band.

In an embodiment, the cover 20 may be made through the following steps, as illustrated in FIGS. 4-9. A pattern 28 is provided. The pattern 28 may generally match the size and shape of a mask 10 to be used with the corresponding mask cover 20. A material, such as a knitted material having a measurable elasticity, may also be provided. Two halves 24, 26 may be cut from the pattern 28. The first half 24 may be cut with the grain in a first direction and the second half 26 may be cut with the grain in a second direction, as illustrated in FIG. 6. Alternatively, the two halves 24, 26 may be cut and arranged with the bias of the first half 24 at an angle, such as perpendicular, to the bias of the second half 26. The two halves 24, 26 may be arranged such that they abut or overlap along their respective inner edges 40, 42. The two material halves 24, 26 may then be sewn together by a seam 34 at a top and bottom portion of the halves 24, 26, as shown in FIG. 8. The portion of the inner edges 40, 42 between the top and bottom ends may be left unconnected to create an opening 22 to allow a user to breathe through the mask cover, thus removing the need for any separate opening to be cut. An elastic band 30 may be placed around an outer perimeter of the cover 20. The outer material may be folded back onto the elastic band 30 and sewn shut to contain the elastic band therein. The mask cover 20 may then be connected to a corresponding mask 10 by expanding the elastic band 30 and placing the cover 20 over the cushion 12. When connected, the cover may stretch to allow the opening 22 to expand and may hold in place to prevent movement or deformation while in use.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

I claim:

1. A CPAP mask cover comprising:
   a first material section having a first orientation;
   a second material section having a second orientation different from said first orientation of the first material section;
   a first seam connecting the first and second material sections along an abutment or overlap of the first and second material section edges, wherein the first seam is located along a first portion of the abutment or overlap at or near a first end of the first and second material sections;
   a second seam connecting the first and second material sections along the abutment or overlap of the first and second material section edges, wherein the second seam is located along a second portion of the abutment or overlap at or near a second end, opposite the first end, of the first and second material sections;
   wherein a third portion of the edges of the first and second material sections between the first and second seams is unconnected and capable of forming an opening when the mask cover is stretched; and
   wherein the orientation of the first material section is substantially perpendicular to the orientation of the second material section.

2. The CPAP mask cover of claim 1, wherein the first and second material sections are formed of a knit or jersey material.

3. The CPAP mask cover of claim 2, wherein the knit or jersey material includes a straight grain and a cross grain, wherein the straight grain and the cross grain are substantially perpendicular, and wherein a bias can be measured as 45 degrees between the straight grain and the cross grain.

4. The CPAP mask cover of claim 3, wherein the bias of the first material section is oriented substantially perpendicular to the bias of the second material section.

5. The CPAP mask cover of claim 1 further comprising an elastic band located at or near an outer edge of the CPAP mask cover.

6. A method of making a CPAP mask cover comprising the steps of:
   providing a pattern for cutting sections of a material;
   cutting a first material section having a first orientation;
   cutting a second material section having a second orientation different from the first orientation of the first material section;
   arranging the first and second material sections such that an inner edge of the first material section abuts or overlaps an inner edge of the second material section;
   forming a first seam along the abutment or overlap of the first and second material sections, wherein the first seam is located along a first portion of the abutment or overlap at or near a first end of the CPAP mask cover;
   forming a second seam along the abutment or overlap of the first and second material sections, wherein the second seam is located along a second portion of the abutment or overlap at or near a second end of the CPAP mask cover, opposite the first end; and
   wherein a third portion of the inner edges of the first and second material sections between the first and second seams remains unconnected and capable of forming an opening when the mask cover is stretched.

7. The method of claim 6 further comprising the step of connecting an elastic band about an outer portion of the CPAP mask cover.

8. The method of claim 6 wherein the orientation of the first material section is substantially perpendicular to the orientation of the second material section.

9. The method of claim 6, wherein the first and second material sections are formed of a knit or jersey material.

10. The method of claim 9, wherein the knit or jersey material includes a straight grain and a cross grain, wherein the straight grain and the cross grain are substantially perpendicular, and wherein a bias can be measured as 45 degrees between the straight grain and the cross grain.

11. The method of claim 10, wherein the bias of the first material section is oriented substantially perpendicular to the bias of the second material section.

\* \* \* \* \*